United States Patent [19]

Hayward

[11] Patent Number: 4,677,132
[45] Date of Patent: Jun. 30, 1987

[54] INHIBITION OF BONE RESORPTION BY ETODOLAC

[75] Inventor: Marshall A. Hayward, Lawrenceville, N.J.

[73] Assignee: American Home Products Corporation (Del.), New York, N.Y.

[21] Appl. No.: 839,013

[22] Filed: Mar. 12, 1986

[51] Int. Cl.$^4$ ............................................. A61U 31/40
[52] U.S. Cl. .................................................... 514/411
[58] Field of Search ........................................ 514/411

[56] References Cited

U.S. PATENT DOCUMENTS 3,939,178  2/1976  Demerson et al. ............. 260/326.28
4,076,831  2/1976  Demerson ....................... 260/326.28
4,533,551  8/1985  Martel ................................. 514/411

OTHER PUBLICATIONS

R. D. Williams et al., Science, 227, 640–642 (1985).
V. Maresca, J. Int. Med. Res. 13, 311–316 (1985).
W. A. Peck et al., J. of the Amer. Med. Assoc., 252, 799–802 (1984).
Ferdinandi et al., J. of Pharm. & Experimental Therepeutics, 220, 417–426 (1982).

Primary Examiner—Stanley J. Friedman
Attorney, Agent, or Firm—John W. Routh

[57] ABSTRACT

A method for modifying the balance between bone production and bone resorption in a host animal by administration of etodolac to inhibit bone resorption.

5 Claims, 3 Drawing Figures

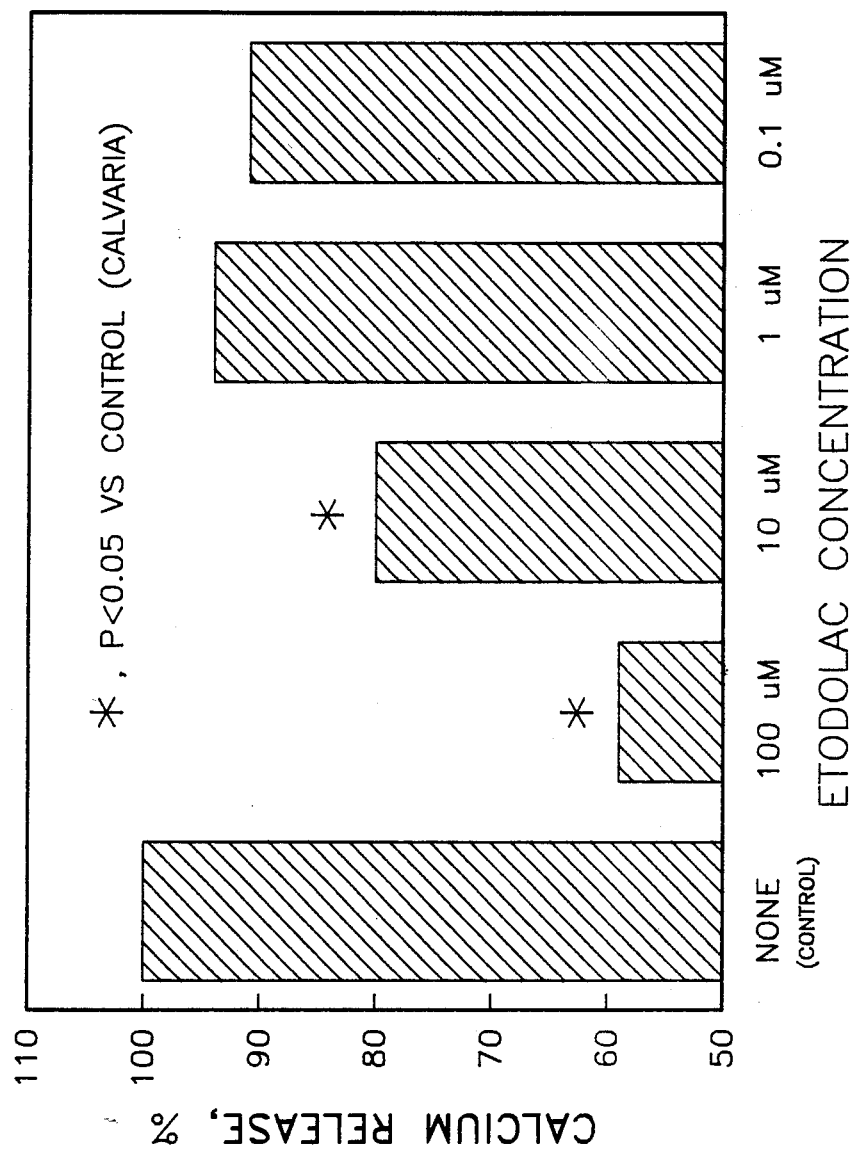

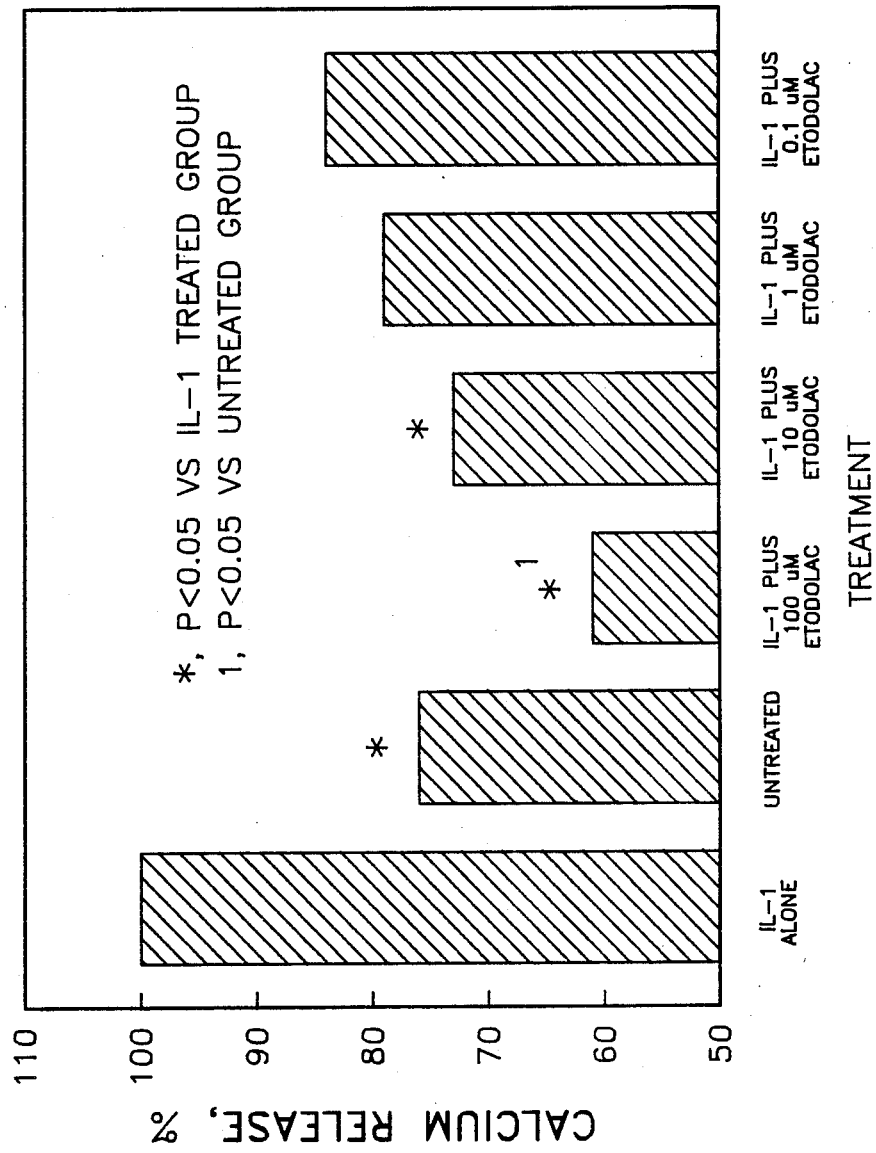

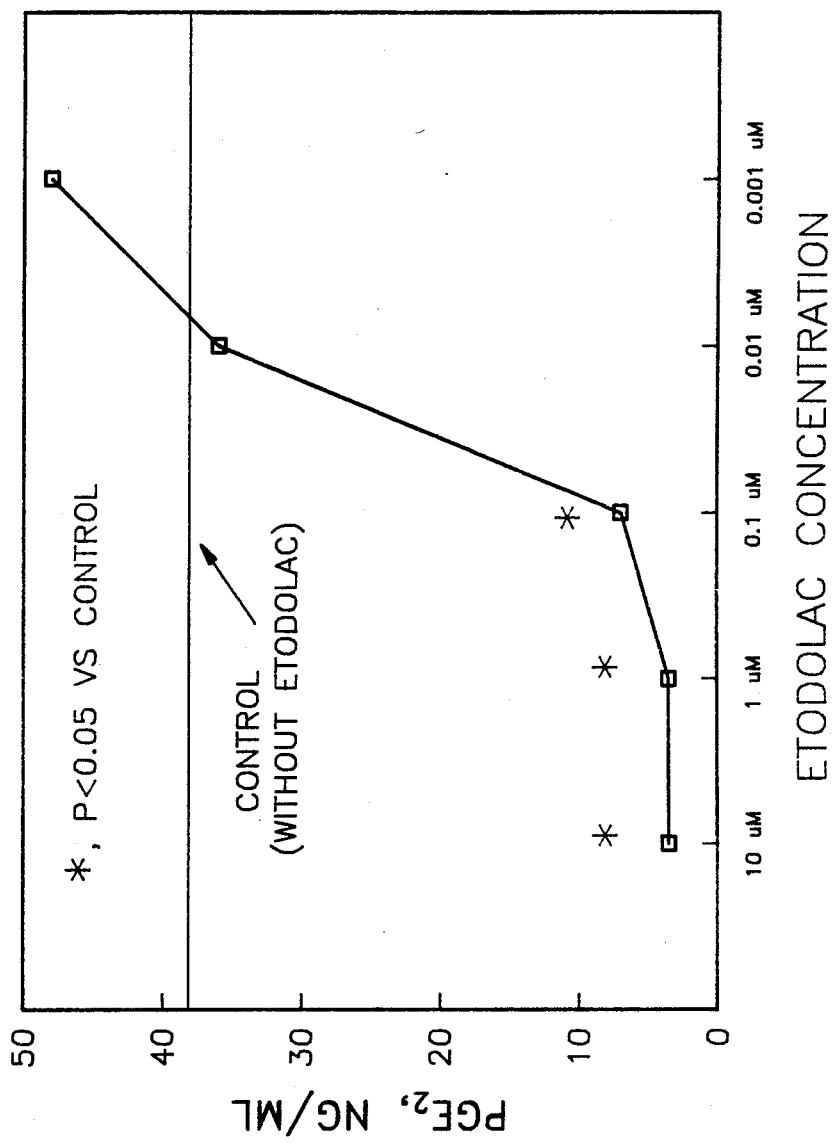

INHIBITION OF BONE RESORPTION BY ETODOLAC

This invention relates to a process for modifying the balance between bone production and bone resorption in a host animal, including man, and more specifically to the use of etodolac for the inhibition of bone resorption.

BACKGROUND OF THE INVENTION

Osteoporosis is a common condition in adults which is evidenced by a decrease in bone density throughout the body. In fact, both the bone mineral (calcium phosphate called "hydroxyapatite") and the matrix (major protein called "collagen") are slowly lost. This condition may begin to occur in humans as early as age 30. In general, the process is more rapid in women than in men. However, after age 80 there is no sex difference in the incidence of osteoporosis. In the course of 10 to 20 years of bone loss there may be symptoms of back pain and X-ray evidence of deformation of the back bone. At older ages, the brittleness of the bones become evident by the ease in which the pelvis and femur fractures and the slowness of their subsequent healing. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, bone resorption exceeds bone formation.

A survey indicates that in the United States there may be four million osteoporotic patients with serious symptoms such as vertebral fractures (D. Whedon, Clinical Endocrinology, II, 349–376 (1968). Moreover, it is estimated that there are currently another 10 million persons suffering from osteoporosis who have not yet developed symptoms. Various types of osteoporosis are designated according to special conditions believed to be causative: senile (aging); post-menopausal (female loss of estrogenesis); disuse (chronic immobilization); steroid (long term steroid treatment as in arthritis). Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorus, Vitamin D, estrogens, calcium salts, fluorides and calcitonin.

Anabolic agents and estrogen replacement therapy have been the therapy of choice for osteoporosis in post-menopausal women. Unfortunately, recent studies have suggested that patients taking only estrogens may have an increased risk of endometriosis. Hence, the advisability of long-term use of such treatment is questioned by some practitioners.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass and it could increase urinary calcium excretion.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include inorganic phosphate type drugs, calcitonin and mithramycin. However, all of these drugs suffer serious drawbacks.

Mithramycin, an antibiotic, has anti-tumor activity together with hypocalcemic activity, effecting a lowering of serum calcium which in turn is believed to be indicative of a decrease in the relative rate of bone resorption—i.e., bone resorption relative to bone production. Side effects, however, include renal and hepatic toxicity as well as nausea. Likewise, the inorganic phosphates (called "phosphonates") have side effects which include extraskeletal calcification, hypotension and renal failure. Calcitonin presents an immunological problem because it is derived from a non-human source. Thus, none of the foregoing agents are at present suitable for use alone in the treatment of osteoporosis.

SUMMARY OF THE INVENTION

It is an object of this invention to provide a method wherein a host animal, including man, suffering from osteoporosis is treated in order to modify the balance between the rates of bone deposition and bone resorption in said host animal whereby the ratio of the latter to the former is reduced.

It is another object of this invention to provide a process for the treatment of a host animal in order to prevent the deterioration of existing healthy bone tissues in said host animal.

It is a further object of this invention to provide a process for the treatment of periodontal disease.

It is yet another object of this invention to provide a treatment for facilitating the healing of damaged bones.

These and other objects are achieved by the practice of this invention which, briefly, comprises administering to a host animal, including man, the compound known generically as etodolac.

Etodolac, 1,8-diethyl-1,3,4,9-tetrahydropyrano[3,4-b]indole-1-acetic acid, is a member of the pyranocarboxylic class of non-steroidal anti-inflammatory agents. Its structure is as follows:

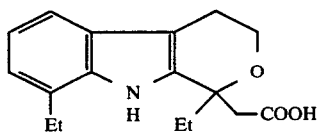

Etodolac has been demonstrated to be a clinically effective analgesic and anti-inflammatory agent, and has been shown to posses an exceptional safety profile with respect to the gastrointestinal tract and renal function. Its preparation is disclosed in U.S. Pat. No. 3,939,178 and compositions for its use are disclosed in U.S. Pat. No. 4,076,831, hereby incorporated herein in their entirety.

Etodolac has also been shown to produce a reversal of the articular pathology associated with arthritis in mammals. Note U.S. Pat. No. 4,533,551.

DETAILED DESCRIPTION OF THE INVENTION

The present invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ratio, of etodolac. The etodolac is usually administered to humans at a daily dose ranging from 200 mg to 1200 mg, preferably in a divided dose of 500 mg twice daily for a total daily dose of 1000 mg.

The advantageous effects of etodolac in preventing bone resorption in accordance with the present invention are demonstrated by the following experimental results.

Etodolac was examined for its effects on isolated bone tissue and primary osteoblast cultures. Bone resorption was measured by determining the amount of calcium-45 released from prelabelled perinatal murine calvaria and ulnae. Effects on osteoblast proliferation and viability were determined by Coulter counter determinations of the cell number content of cultures and by assessing cellular protein content colorimetrically. Etodolac significantly inhibited bone resorption at concentrations as low as 10-6M in vitro. Etodolac had no diminutive effect on osteoblast-like cell proliferation or protein synthesis at concentrations as high as 10-4M in vitro. Etodolac significantly lowered the $PGE_2$ content of explant culture medium. Interleukin-1 (IL-1) stimulated bone resorption was inhibited by etodolac, in a test of efficacy under conditions in which bone resorption is elevated relative to control levels. Etodolac inhibits both endogenous and IL-1 stimulated bone resorption by a mechanism which is not related to decreased cell viability but which is correlated with the PGE2 content of cultures.

EXAMPLE 1

$^{45}$Ca-release in vitro bone resorption assay

This assay was performed according to the standard procedure described in articles by Eilon G, Raisz L G: "Comparison of the effects of stimulators and inhibitors of resorption on the release of lysosomal enzymes and radioactive calcium from fetal bone in organ culture". Endocrinology 1978; 103: 1969-1975, and Dominguez J H, Raisz L G "Effects of changing hydrogen ion, carbonic acid, and bicarbonate concentrations on both resorption in vitro" Calcif. Tissue Int. 29: 7-13 (1979).

Bone resorption was assayed by measuring the amount of $^{45}$Ca released from pre-labeled murine calvaria and ulnae cultured in vitro. Rat dams were injected s.c. with 100 microCuries of $^{45}$Ca (New England Nuclear) on day 18 of pregnancy. Pups were ablated and dissected free of soft tissue on day 20 of gestation. Calvaria were bisected along the sagittal suture, and the cartilagenous ends of ulnae were removed. Bones were randomized into groups of eight, and one group, selected as a devitalized control, was heated at 60° C. for 90 min.

Explanted bones were cultured in BGJ (Fitton-Jackson modification) containing 2% fetal bovine serum in a humidified 5% $CO_2$ atmosphere at 37° C. The media contained antibiotic supplements (penicillin, streptomycin, and fungizone) at recommended dosages. After 24 hours of culture to allow any nonspecifically associated $^{45}$Ca to dissociate from the explants, the medium was replaced with control medium or medium containing etodolac. Bones were incubated for an additional 72 hours, then a medium aliquot was removed for quantitation of $^{45}$Ca content via scintillation spectrometry. Bones were removed from media, rinsed in phosphate buffered saline, hydrolyzed with 6N HCl, neutralized with NaOH, and $^{45}$Ca content quantified as described above. The amount of $^{45}$Ca released from bones during the 72 hour culture period was determined by calculating the amount of $^{45}$Ca present in the bone at the initiation of drug treatment, and determining the percent Ca released into the media during this period. Statistical significance testing among groups was performed via SAS (SAS User's Guide, SAS Intitute, Cary, N.C.). The amount of $^{45}$Ca released during the culture period was taken as an index of bone resorption.

$^{45}$Ca release from cultured perinatal bone explants (both calvaria and long bones) was inhibited by etodolac. Significant inhibition (P<0.05 vs control) was observed at $10^{-4}$ and $10^{-5}$ molar etodolac in calvarial cultures and in long bone (ulnae) cultures. The pertinent data are summarized in Table 1. In all experiments, the background $^{45}$Ca release from parallel devitalized cultures was substracted before the percent $^{45}$Ca release was calculated in order that only $^{45}$Ca release occurring by metabolic activity is assessed. A lower value represents greater inhibition of bone resorption.

Etodolac inhibited bone resorption in a concentration dependent manner at concentrations as low as 1 μM in vitro (Ulnae: 76%, 78%, and 86% of control $^{45}$Ca release at 100, 10, and 1 μM respectively; Calvaria, 59% and 80% of control at 100 and 10 μM respectively; all P<0.05, n=8 bones/group).

The results are shown in FIG. 1 of the drawings which plots % calcium release versus etodolac concentration.

TABLE 1

Effect of etodolac and other anti-inflammatory standards on $^{45}$Ca release from cultured murine bone explants. Results are presented as percent inhibition of control $^{45}$Ca release.

| | Test Compound Concentration | | | | |
|---|---|---|---|---|---|
| Molar | Calvaria Etodolac | Calvaria Flurbiprofen | Calvaria Naproxen | Calvaria Piroxicam | Ulnae Etodolac |
| $10^{-4}$ | 59* | 72* | 71* | 70* | 76* |

TABLE 1-continued

Effect of etodolac and other anti-inflammatory standards on $^{45}$Ca release from cultured murine bone explants. Results are presented as percent inhibition of control $^{45}$Ca release.

| Molar | Test Compound Concentration | | | | |
|---|---|---|---|---|---|
| | Calvaria Etodolac | Calvaria Flurbi-profen | Calvaria Naproxen | Calvaria Piroxicam | Ulnae Etodolac |
| $10^{-5}$ | 80* | 77* | N.D. | N.D. | 78* |

*Significant at P < 0.05 vs control, Dunnett's test.
N.D. = Not significantly different from control.

EXAMPLE 2

Interleukin-1 (IL-1) Stimulated Bone Resorption And PGE2 Production

This assay was performed in accordance with the same standard procedure as that of Example 1 except that IL-1 (Genzyme) was included in the cultures as described above in addition to etodolac. The results are shown in FIG. 2 of the drawings wherein calcium release is plotted versus etodolac concentration.

Prostaglandin $E_2$ synthesis was determined by analyzing the media from cultured bone explants for $PGE_2$ content with an ELISA assay. Monoclonal antibodies to $PGE_2$ were incubated with 100 microliters of culture medium for 2 hours at 4 deg C. Concomitantly, 96 well microtiter plate wells were coated with $PGE_2$ conjugated to Bovine Serum Albumin (4 deg C., 15 hours). 100 microliters of the mouse antibody-test medium incubation mixture was added to each well, and the plate was incubated for 2 hours at 4 deg C. Wells were rinsed, then goat-anti-mouse antibody conjugated to alkaline phosphatase was added to each well. After 45 minutes at room temperature, wells were rinsed and 200 microliters of 1 mg/ml p-nitrophenyl acetate was added to each well. After 20 minutes at room temperature, the absorbance of the chromogenic p-nitrophenol solution in each well was quantified in an automated plate reader at 405 nm to determine p-nitrophenol formation, as an index of alkaline phosphatase activity, which may be correlated with the amount of $PGE_2$ in the original media sample.

The results are shown in FIG. 3 of the attached drawings in which $PGE_2$ production (as determined by measuring the $PGE_2$ content of cultures at the time bone resorption was measured) is plotted versus the etodolac concentration of the treated groups. Statistical significance versus the IL-1 treated group is indicated as follows: (*=P<0.05; Dunnett's Test).

Etodolac significantly decreased the $PGE_2$ content of explant culture medium at concentrations as low as 0.1M in vitro; however, bone resorption was not inhibited by these concentrations of etodolac. Interleukin-1 (IL-1) stimulated bone resorption and $PGE_2$ production in calvaria explants ($PGE_2$ content determined via ELISA). $PGE_2$ production in IL-1 treated cultures was decreased 80% by etodolac at concentrations as low as 1 $\mu$M (significantly lower than control cultures, P<0.05); however, treatment with 10 $\mu$M etodolac was necessary to achieve a statistically significant reduction of bone resorption in the presence of IL-1.

EXAMPLE 3

Osteoblast proliferation, in vitro

This assay was carried out according to previously described procedures set forth in three journal articles as follows:

Dziak R, Brand J S: "Calcium transport in isolated bone cells. I. Bone cell isolation procedures". J. Cell Physiol 1974; 84: 75–83, Puzas J E, Drivdahl R H, Howard G A, et al: "Endogenous inhibitor of bone cell proliferation". Proc. Soc. Exp. Biol. Med. 1981; 166: 113–112.

Kream B E, Smith M D, Canalia E, Raisz L G "Characterization of the effect of insulin on collagen synthesis in fetal rat bone". Endocrinology 1985; 116: 296–302.

Briefly, osteoblasts and pre-osteoblasts were isolated from 20-day old embryonic rat calvaria by enzymatic digestion of the extracellular matrix using collagenase (2 mg/ml). The cells were plated at 250 cells/mm$^2$ and incubated at 37° C. in BGJ$_b$ media containing 5% (v/v) fetal bovine serum (FBS) in 24-well culture plates and 96-well microplates. After 48 hours, the media and all nonadherent cells were drawn off and replaced with fresh BGJ$_b$+5% FBS media containing final concentrations of etodolac of $1\times10^{-4}$, $1\times10^{-5}$, $1\times10^{-6}$ and $1\times10^{-7}$M. Control cultures of cells, without added etodolac, were also incubated in parallel. After 96 hrs. the media was drawn off, and the cells rinsed with phosphate-buffered saline.

The cells in the 24-well plates were removed from the plates with 0.33% trypsin-EDTA (GIBCO), and cell number was determined using a Coulter counter. The rinsed cells in the 96-well plates were further incubated at 55° C. for 60 minutes with Pierce BCA-protein reagent; then the absorbance at 595 nm was determined with Pierce Chemical Co, BCA Protein Assay No. 23225, 1984.

Using a standard protein curve at A$_{595}$ nm vs g of protein, total protein per well was thus determined as an index of cell proliferation. Neither protein synthesis nor cell proliferation was modulated by etodolac treatment of cultured murine osteoblasts.

Etodolac had no diminutive effect on osteoblast proliferation or protein synthesis at concentrations as high as 100 $\mu$M in vitro, indicating that bone resorption was not related to acute toxicity.

Statistical testing was performed via STAT 80 (Student's t-test; STAT 80 User's Guide, Statware, Salt Lake City, Utah).

Etodolac pharmacologically inhibits bone resorption in both untreated and IL-1 stimulated bone explants by a mechanism which is not related to decreased cell viability and which is not a direct consequence of cyclooxygenase inhibition.

Etodolac has pharmacologic effects on bone which are consistent with other standard compounds with established anti-inflammatory activity. While etodolac neither directly inhibits carbonic anhydrase nor stimulates osteoblast proliferation, it does have the ability to inhibit bone resorption in vitro. $PGE_2$ has been demonstrated to be a stimulator of bone resorption in vitro. Note the article by Dietrich J W, Goodson J M, Raisz L G: "Stimulation of bone resorption by various prostaglandins in organ culture". Prostaglandins 1975; 10: 231–240.

Edotolac has the ability differentially to inhibit formation of $PGE_2$ ["Disposition of Etodolac, other anti-inflammatory Pyranoindole-1-Acetic-Acids and Furobufen in normal and Adjuvant arthritic rats", Ferdinandi et al, J. of Pharmacology and Experimental Therapeutics, 1982 220, 417–426] and hence the data are consistent with the pharmacologic profile of etodolac to impact favorably upon bone resorption.

Indomethacin also significantly lowered control bone resorption, but not resorption stimulated by $PGE_2$, PTH, or 1,25-dihydroxyvitamin D in newborn mouse calvaria as discussed in an article by Minkin C, Fredricks R S, Pokress S, et al: Bone resorption and humoral hypercalcemia of malignancy: Stimuation of bone resorption in vitro by tumor extracts is inhibited by prostaglandin synthesis inhibitors. J Clin Endocrinol Metab 1981; 53: 941–947.

Very little other in vitro bone resorption data has been reported with other non-steroidal anti-inflammatory compounds listed in Table 1. Indomethacin, with mixed results, as well as flurbiprofen have ben used in vivo as inhibitors of alveolar bone loss in peridontal disease. Note the article by Williams R C: "The use of non-steroidal anti-inflammatory drugs in periodontal disease", in "New Anti-Inflammatory Drugs: Mechanisms and Clinical Use", Lewis A J, Furst D E, eds., New York, Marcel Dekker, 1985, in press.

The administration of etodolac in accordance with this invention can be supplemental to other regimens for the treatment of osteoporosis or periodontitis. For example, the administration of etodolac can be supplemental to the 600 mg to 1200 mg daily intake of calcium as calcium phosphate or calcium carbonate. Also, the administration of etodolac can be supplemental to estrogen replacement therapy such as 0.625 mg daily of conjugated equine estrogen.

I claim:

1. A method for the treatment of a host animal suffering from a disease state evidenced by elevated bone loss in order to modify the balance between the rate of bone resorption and the rate of bone formation in said host animal whereby the ratio of said rate of bone resorption to said rate of bone formation is reduced, comprising administering to said host animal an amount of etodolac sufficient to modify said balance and reduce said ratio.

2. The method of claim 1 wherein the etodolac is administered at a daily dose ranging from 200 mg to 1200 mg.

3. The method of claim 2 wherein the etodolac is administered at a dose of 500 mg twice daily for a total daily dose of 1000 mg.

4. The method of claim 1 wherein the host animal suffers from osteoporosis.

5. The method of claim 1 wherein the host animal suffers from periodontal disease.

* * * * *